US009839667B2

(12) United States Patent
Feinerman et al.

(10) Patent No.: US 9,839,667 B2
(45) Date of Patent: Dec. 12, 2017

(54) PREVENTION AND TREATMENT OF OCULAR SIDE EFFECTS WITH A CYCLOSPORIN

(71) Applicant: Allergan, Inc., Irvine, CA (US)

(72) Inventors: Gregg Feinerman, Irvine, CA (US); Neil Barth, Newport Beach, CA (US); Rhett Schiffman, Laguna Beach, CA (US); Pamela S. Barnett, Aliso Viejo, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/957,858

(22) Filed: Aug. 2, 2013

(65) Prior Publication Data

US 2014/0038905 A1 Feb. 6, 2014

Related U.S. Application Data

(60) Continuation-in-part of application No. 12/825,116, filed on Jun. 28, 2010, now Pat. No. 8,501,174, which is a division of application No. 11/548,631, filed on Oct. 11, 2006, now Pat. No. 7,745,400.

(60) Provisional application No. 60/596,709, filed on Oct. 14, 2005, provisional application No. 60/597,431, filed on Nov. 30, 2005, provisional application No. 60/805,577, filed on Jun. 22, 2006.

(51) Int. Cl.
*A61K 31/7072* (2006.01)
*A61K 38/13* (2006.01)
*A61K 45/06* (2006.01)
*A61K 31/337* (2006.01)
*A61K 36/13* (2006.01)

(52) U.S. Cl.
CPC ............ *A61K 38/13* (2013.01); *A61K 31/337* (2013.01); *A61K 31/7072* (2013.01); *A61K 36/13* (2013.01); *A61K 45/06* (2013.01)

(58) Field of Classification Search
CPC .... A61K 38/13; A61K 31/7072; C07K 7/645; C07H 19/067
See application file for complete search history.

(56) References Cited

U.S. PATENT DOCUMENTS

| 4,388,229 | A | 6/1983 | Fu |
|---|---|---|---|
| 4,388,307 | A | 6/1983 | Cavanak |
| 4,649,047 | A | 3/1987 | Kaswan |
| 4,814,323 | A | 3/1989 | Andrieu et al. |
| 4,839,342 | A | 6/1989 | Kaswan |
| 4,996,193 | A | 2/1991 | Hewitt et al. |
| 5,047,396 | A | 9/1991 | Orban et al. |
| 5,051,402 | A | 9/1991 | Kurihara et al. |
| 5,294,604 | A | 3/1994 | Nussenblatt |
| 5,296,158 | A | 3/1994 | MacGilp et al. |
| 5,342,625 | A | 8/1994 | Hauer et al. |
| 5,411,952 | A | 5/1995 | Kaswan |
| 5,474,979 | A | 12/1995 | Ding et al. |
| 5,543,393 | A | 8/1996 | Kim et al. |
| 5,589,455 | A | 12/1996 | Woo |
| 5,614,491 | A | 3/1997 | Walch et al. |
| 5,639,724 | A | 6/1997 | Cavanak |
| 5,652,212 | A | 7/1997 | Cavanak et al. |
| 5,753,166 | A | 5/1998 | Dalton et al. |
| 5,759,997 | A | 6/1998 | Cavanak |
| 5,766,629 | A | 6/1998 | Cho et al. |
| 5,798,333 | A | 8/1998 | Sherman |
| 5,827,822 | A | 10/1998 | Floc'h et al. |
| 5,827,835 | A | 10/1998 | Kabra |
| 5,834,017 | A | 11/1998 | Cho et al. |
| 5,891,846 | A | 4/1999 | Ishida et al. |
| 5,916,589 | A | 6/1999 | Hauer et al. |
| 5,951,971 | A | 9/1999 | Kawashima et al. |
| 5,962,014 | A | 10/1999 | Hauer et al. |
| 5,962,017 | A | 10/1999 | Hauer et al. |
| 5,962,019 | A | 10/1999 | Cho et al. |
| 5,977,066 | A | 11/1999 | Cavanak |
| 5,977,067 | A | 11/1999 | Evers et al. |
| 6,007,840 | A | 12/1999 | Hauer et al. |
| 6,024,978 | A | 2/2000 | Hauer et al. |
| 6,057,289 | A | 5/2000 | Mulye |
| 6,190,691 | B1 | 2/2001 | Mak |
| 6,197,335 | B1 | 3/2001 | Sherman |
| 6,245,805 | B1 | 6/2001 | Broder et al. |
| 6,254,860 | B1 | 7/2001 | Garst |
| 6,254,885 | B1 | 7/2001 | Cho et al. |

(Continued)

FOREIGN PATENT DOCUMENTS

| EP | 0146341 | 12/1984 |
|---|---|---|
| EP | 0471293 | 2/1992 |

(Continued)

OTHER PUBLICATIONS

Zapata et al. Sjogren Keratoconjunctivitis Sicca Treated With Rituximab. Cornea. Aug. 2007, vol. 26, No. 7, pp. 886-887.*
Mikhail et al. Safety of capecitabine: a review. Expert Opinion on Drug Safety. 2010, vol. 9, No. 5, pp. 831-841.*
Park et al. Abstract LB-172: A randomized phase II study of S-1 versus capecitabine . . . Cancer Research. Apr. 15, 2013, vol. 73, No. 8, Supplement, LB-172.*
Van Cutsem et al. Capecitabine, an Oral Fluoropyrimidine Carbamate With Substantial Activity in Advanced Colorectal Cancer . . . Journal of Clinical Oncology. Mar. 2000, vol. 18, No. 6, pp. 1337-1345.*

(Continued)

*Primary Examiner* — Jeffrey E Russel
(74) *Attorney, Agent, or Firm* — Laura L. Wine

(57) ABSTRACT

The present disclosure relates to methods of treatment or prevention of ocular conditions caused by treatment with certain therapeutically active agents. The methods can include administering a cyclosporine, an analog or derivative thereof, or a combination thereof to an eye of a mammal suffering from an ocular condition cased by treatment with certain therapeutically active agents, which can include a chemotherapy agent or an antiviral agent.

6 Claims, No Drawings

(56) References Cited

U.S. PATENT DOCUMENTS

| | | | |
|---|---|---|---|
| 6,267,985 B1 | 7/2001 | Chen et al. | |
| 6,284,268 B1 | 9/2001 | Mishra et al. | |
| 6,294,192 B1 | 9/2001 | Patel et al. | |
| 6,306,825 B1 | 10/2001 | Cavanak | |
| 6,350,442 B2 | 2/2002 | Garst | |
| 6,395,770 B1 | 5/2002 | Broder et al. | |
| 6,420,355 B2 | 7/2002 | Richter et al. | |
| 6,468,968 B2 | 10/2002 | Cavanak et al. | |
| 6,475,519 B1 | 11/2002 | Meinzer et al. | |
| 6,486,124 B2 | 11/2002 | Olbrich et al. | |
| 6,569,463 B2 | 5/2003 | Patel et al. | |
| 6,582,718 B2 | 6/2003 | Kawashima et al. | |
| 6,638,522 B1 | 10/2003 | Mulye | |
| 6,656,504 B1 | 12/2003 | Bosch et al. | |
| 6,720,001 B2 | 4/2004 | Chen et al. | |
| 6,723,339 B2 | 4/2004 | Meinzer et al. | |
| 6,787,306 B1 | 9/2004 | Gonzalez et al. | |
| 6,916,785 B2 | 7/2005 | Patel | |
| 7,141,576 B2 | 11/2006 | Lackey et al. | |
| 7,202,209 B2 | 4/2007 | Olejnik et al. | |
| 7,276,476 B2 | 10/2007 | Olejnik et al. | |
| 7,288,520 B2 | 10/2007 | Olejnik et al. | |
| 7,297,679 B2 | 11/2007 | Olejnik et al. | |
| 7,501,393 B2 | 3/2009 | Chang et al. | |
| 7,745,400 B2 | 6/2010 | Feinerman et al. | |
| 8,501,174 B2 * | 8/2013 | Feinerman et al. | ....... 424/133.1 |
| 2001/0003589 A1 | 6/2001 | Neuer et al. | |
| 2001/0036449 A1 | 11/2001 | Garst | |
| 2001/0041671 A1 | 11/2001 | Napoli | |
| 2002/0012680 A1 | 1/2002 | Patel et al. | |
| 2002/0013272 A1 | 1/2002 | Cavanak et al. | |
| 2002/0016290 A1 | 2/2002 | Floc'h et al. | |
| 2002/0016292 A1 | 2/2002 | Richter et al. | |
| 2002/0025927 A1 | 2/2002 | Olbrich et al. | |
| 2002/0025943 A1 | 2/2002 | Bradley et al. | |
| 2002/0045601 A1 | 4/2002 | Kawashima et al. | |
| 2002/0081338 A1 | 6/2002 | MacKeen | |
| 2002/0107183 A1 | 8/2002 | Petswzulat et al. | |
| 2002/0119190 A1 | 8/2002 | Meinzer et al. | |
| 2002/0165134 A1 | 11/2002 | Richter et al. | |
| 2003/0060402 A1 | 3/2003 | Cavanak et al. | |
| 2003/0083366 A1 | 5/2003 | Grove et al. | |
| 2003/0108626 A1 | 6/2003 | Benita et al. | |
| 2003/0133984 A1 | 7/2003 | Ambuhl et al. | |
| 2003/0143250 A1 | 7/2003 | Hauer et al. | |
| 2003/0147954 A1 | 8/2003 | Yang et al. | |
| 2003/0158249 A1 | 8/2003 | Chi et al. | |
| 2003/0166507 A1 | 9/2003 | Li et al. | |
| 2003/0166517 A1 | 9/2003 | Fricker et al. | |
| 2003/0191179 A1 | 10/2003 | Joshi-Hangal et al. | |
| 2003/0211983 A1 | 11/2003 | Petszulat et al. | |
| 2003/0212090 A1 | 11/2003 | Chen et al. | |
| 2003/0215496 A1 | 11/2003 | Patel et al. | |
| 2003/0216431 A1 * | 11/2003 | Raut | ............................ 514/313 |
| 2003/0225011 A1 | 12/2003 | David et al. | |
| 2004/0048789 A1 | 3/2004 | Patel | |
| 2004/0076691 A1 | 4/2004 | Haines et al. | |
| 2004/0092435 A1 | 5/2004 | Peyman | |
| 2004/0101552 A1 | 5/2004 | Patel | |
| 2004/0102366 A1 | 5/2004 | Patel | |
| 2004/0106546 A1 | 6/2004 | Napoli | |
| 2004/0161458 A1 | 8/2004 | Meinzer et al. | |
| 2004/0167063 A1 | 8/2004 | Cavanak et al. | |
| 2004/0185068 A1 | 9/2004 | Yu et al. | |
| 2004/0198645 A1 | 10/2004 | Ambuhl et al. | |
| 2005/0013854 A1 | 1/2005 | Mannino et al. | |
| 2005/0025810 A1 | 2/2005 | Peyman | |
| 2005/0043258 A1 | 2/2005 | Bennett et al. | |
| 2005/0048087 A1 | 3/2005 | Posanski | |
| 2005/0059583 A1 | 3/2005 | Acheampong et al. | |
| 2005/0085438 A1 | 4/2005 | Cardozo et al. | |
| 2005/0118254 A1 | 6/2005 | Choi et al. | |
| 2005/0129718 A1 | 6/2005 | Sherman | |
| 2005/0147659 A1 | 7/2005 | Carli et al. | |
| 2005/0196370 A1 | 9/2005 | Yu et al. | |
| 2005/0272755 A1 | 12/2005 | Denis et al. | |
| 2005/0272758 A1 | 12/2005 | Bayever et al. | |
| 2005/0282734 A1 | 12/2005 | Kadima et al. | |
| 2006/0018910 A1 | 1/2006 | Gualberto et al. | |
| 2006/0046993 A1 | 3/2006 | Forino et al. | |
| 2006/0160074 A1 | 7/2006 | Dorn et al. | |
| 2006/0183883 A1 | 8/2006 | Hummel et al. | |
| 2006/0253263 A1 | 11/2006 | Meshkin | |
| 2007/0015691 A1 | 1/2007 | Chang et al. | |
| 2008/0009437 A1 | 1/2008 | Xia et al. | |
| 2008/0305994 A1 | 12/2008 | Zhang et al. | |
| 2010/0021420 A1 | 1/2010 | Lyons et al. | |
| 2010/0166699 A1 | 7/2010 | Thompson et al. | |
| 2011/0159111 A1 * | 6/2011 | Curry et al. | .................. 424/649 |
| 2012/0100133 A1 * | 4/2012 | Fisson et al. | .............. 424/133.1 |
| 2012/0309683 A1 | 12/2012 | Coy et al. | |
| 2013/0252997 A1 | 9/2013 | Schiffman | |

FOREIGN PATENT DOCUMENTS

| | | |
|---|---|---|
| EP | 0547229 | 6/1992 |
| EP | 956853 | 5/1999 |
| WO | WO00/00179 | 1/2000 |
| WO | WO/0008085 | 2/2000 |
| WO | WO01/32142 | 5/2001 |
| WO | 2006015075 A1 | 2/2006 |
| WO | WO2007-047334 | 4/2007 |

OTHER PUBLICATIONS

Benitez, et al., "Influence of topical Cyclosporine A and dissolvent on corenal epithelium permeability of flurorescein," Ophthalmologica 91: 49-55, 1995.

Castillo, et al., "Influence of topical Cyclosporine A and dissolvent on corneal epithelium permeability of fluorescein," Documenta Ophthalmologica, 1995, 91, 49-55.

http:/thornleycompany.com/Products/PEGsters.htm, (2006).

Kuwano et al, "Cyclosporine A Formulation Affects Its Ocular Distribution in Rabbits", Pharmaceutical Research, vol. 19, No. 1, Jan. 2002, 108-111.

Lanzetta et al, "Major ocular complications after organ transplantation", Transplantation Proceedings, vol. 36, No. 10, Dec. 1, 2004, pp. 3046-3048.

TheMerckIndex Results-Form View, Monograph number: 07664, Titles: Polysorbates, 1 page, and Polyoxyethylene, 1 page, (2006).

Pijpe et al. Rituximab Treatment in Patients With Primary Sjogren's Syndrome. Arthritis & Rheumatism. Sep. 2005, vol. 52, No. 9, pp. 2740-2750.

Questions and Answers About Taxotere Injection Concentrate, Patient Information Leaflet by Aventis Pharmaceuticals Inc., Rev. May 2004.

Restasis® Package Insert, (cyclosporine ophthalmic emulsion)0.05%, Sterile, Preserviatve-Free, 2 page, 2004.

Rita, Ritabate 40, INCI Nomenclature (formerly CTFA) . . . Polysorbate 40, 1 page, 1994.

Rita, Ritabate 60, INCI Nomenclature (formerly CTFA) . . . Polysorbate 60, 1 page, (not dated).

Rita, Ritabate 20, INCI Nomenclature (formerly CTFA) . . . Polysorbate 20, 1 page, 1994.

Sandimmue® Package Insert, (cyclosporine oral solution), RxList, The Internet Drug Index, 3pp—2006.

Uniqema, Tween™ Series. Polyoxyethylene derivatives of sorbitan esters. 2 pages.

www.lipochemicals.com document on Emulsifiers and Emulsifying systems (Aug. 20, 2002), pp. 1-5.

U.S. Appl. No. 60/727,684, filed Oct. 17, 2005.

U.S. Appl. No. 11/181,509, filed Jul. 13, 2005.

Akpek, Esen Karamursel et al, A Randomized Trial of Topical Cyclosporin 0.05% in Topical Steroid-Resistant Atopic Keratoconjunctivitis, Ophthalmology, 2004, 476-482, 111.

Schmid, et al., Update on Ocular Complications of Systemic Cancer Chemotherapy, Survey of Ophthalmology, Feb. 2006, pp. 19-40, vol. 51, No. 1.

(56) References Cited

OTHER PUBLICATIONS

Calonge, Margarita, The Treatment of Dry Eye, Survey of Ophthalmology, 2001, S227-S239, vol. 45, Supplement 2, Elsevier Science, Inc.

Fraunfelder, Frederick T., et al., The Role of Medications in Causing Dry Eye, Journal of Ophthalmology, Jan. 2012, 197-198, vol. 99, No. 2.

* cited by examiner

PREVENTION AND TREATMENT OF OCULAR SIDE EFFECTS WITH A CYCLOSPORIN

CROSS-REFERENCE TO RELATED APPLICATIONS

This application is a continuation-in-part of U.S. patent application Ser. No. 12/825,116, filed Jun. 28, 2010, now U.S. Pat. No 8,501,174, which is a divisional of U.S. patent application Ser. No. 11/548,6311, filed Oct. 11, 2006, now U.S. Pat. No. 7,745,400, which claims priority to U.S. Provisional Application No. 60/596,709, filed Oct. 14, 2005, U.S. Provisional Patent Application No. 60/597,431, filed on Nov. 30, 2005, and U.S. Provisional Patent Application No. 60/805,577, filed on Jun. 22, 2006, all of which are expressly incorporated by reference herein.

DESCRIPTION OF THE INVENTION

Patients undergoing treatment with certain therapeutically active agents can have certain ocular conditions as a result of that treatment. In particular, patients undergoing chemotherapy with a therapeutically active agent effective for treatment of a cancer often have ocular conditions as a result of that treatment.

One embodiment is a method comprising administering a cyclosporin, an analog or derivative thereof, or a combination thereof, to an eye of a mammal in combination with administration of a therapeutically active agent to said mammal, said therapeutically active agent being an chemotherapy agent or an antiviral agent, wherein said method is effective in preventing or treating an ocular condition associated with the use of said therapeutically active agent.

"Administration of a therapeutically active agent to said mammal" means administration of the therapeutically active agent to the mammal in any way that a therapeutically active agent may be administered. Thus, administration of the therapeutically active agent is not limited to the eye, but may include systemic administration via oral, intravenous, rectal, or other means; or administration locally to any part of the body by injection, implantation, topical administration, or other means.

Administration of the therapeutically active agent need not exactly overlap in time with the administration of the cyclosporin, an analog or derivative thereof, or a combination thereof. For example, the cyclosporin, analog or derivative thereof, or a combination thereof might be administered to a mammal before the mammal receives any of the therapeutically active agent to avoid the onset of the ocular condition. In another example, the cyclosporin, analog or derivative thereof, or a combination thereof, might be administered after the mammal has begun to receive the therapeutically active agent. In another example, the cyclosporin, analog or derivative thereof, or a combination thereof, might be administered after the mammal has ceased receiving the therapeutically active agent. Administration of the cyclosporin, analog or derivative thereof, or a combination thereof might also be simultaneous with the administration of the therapeutically active agent. Thus, any time relationship may exist between the mammal receiving the therapeutically active agent and the cyclosporin, analog or derivative thereof, or a combination thereof, provided that the use of the latter is reasonably related to treatment or prophylaxis of a condition associated with the former.

It may be convenient to provide a single pharmaceutical composition which comprises both (i) the cyclosporin, analog or derivative thereof, or a combination thereof and (ii) the therapeutically active agent when the agents are to be administered simultaneously.

It may be convenient to provide (i) the cyclosporin, analog or derivative thereof, or a combination thereof and (ii) the therapeutically active agent in form of a kit. For example, the agents may be packaged together. For example, (i) the cyclosporin, analog or derivative thereof, or a combination thereof and (ii) the therapeutically active agent may each be packaged in conventional pharmaceutical packaging such as boxes, jars, blister packs, vials, bottles, syringes etc., and the individually packaged components may then be combined to form a kit e.g. by the use of further packaging such as a box, or by joining up the individual packages. When in kit form, the agents can be taken independently of one another, thus allowing the user freedom to decide the temporal relationship between his use of each of the agents.

Use of a cyclosporin, or an analog or derivative thereof, including cyclosporin A, for the treatment of ocular conditions occurring in a person undergoing treatment with a therapeutically active agent for the treatment of cancer is contemplated. Accordingly, a particular patient group which may benefit from the present invention is that of persons having ocular conditions resulting from the use of a chemotherapy agent.

Also contemplated is use of a cyclosporin, or an analog or derivative thereof, including cyclosporin A, for the treatment of ocular conditions occurring in a person who is undergoing treatment with an antiviral agent. Accordingly, a particular patient group which may benefit from the present invention is that of persons having ocular conditions resulting from the use of an antiviral agent.

Also contemplated is use of a cyclosporin, or an analog or derivative thereof, including cyclosporin A, for the treatment of ocular conditions occurring in a person who is undergoing treatment with an immunomodulator. Accordingly, a particular patient group which may benefit from the present invention is that of persons having ocular conditions resulting from the use of an immunomodulator.

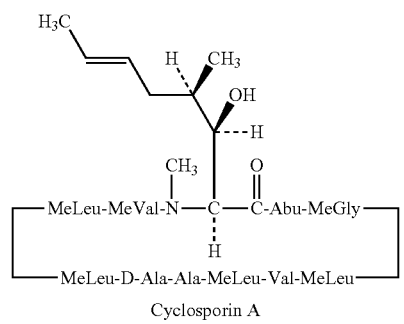

Cyclosporin A

Cyclosporin A is a cyclic peptide with immunosuppressive properties having the structure shown above. It is also known by other names including cyclosporine, cyclosporine A, ciclosporin, and ciclosporin A.

Other cyclosporins include cyclosporine b, cyclosporine D, cyclosporine G, which are well known in the art. Cyclosporin derivatives and analogs are also known in the art. For example, U.S. Pat. Nos. 6,254,860 and 6,350,442, incorporated by reference herein, illustrate several examples. The ocular conditions to be prevented or treated are well known in the art.

In particular, nasolacrimal stenosis, chemotherapy induced ocular toxicity, lacrimal duct stenosis, punctal stenosis, lacrimation, abnormal lacrimation, (such as tear production that is presumed to be suppressed due to ocular inflammation associated with keratoconjunctivitis sicca), increased tearing, nasolacrimal blockage, keratitis, keratoconjunctivitis, conjunctivitis, or a combination thereof may be prevented or treated. Hence, for example, in one embodiment one administers cyclosporin A to a mammal, in combination with administration of a therapeutically active agent to said, to increase tear production that is presumed to be suppressed due to ocular inflammation associated with keratoconjunctivitis sicca to the mammal, wherein "administration of a therapeutically active agent to said mammal" is as defined above; that is, the cyclosporin A may be administered to the mammal before the mammal receives any of the therapeutically active agent, after the mammal begins to receive the therapeutically active agent, or after the mammal ceases receiving the therapeutically active agent.

Also contemplated is a method comprising administering cyclosporin A topically to the eye of a person, wherein docetaxel is also administered to said person, wherein said method is effective in preventing or treating an ocular condition associated with the administration of docetaxel.

Although the ocular condition may be associated with any antiviral agent, the following
antiviral agents are contemplated in particular:
Zalcitabine, and
Rimantadine Hydrochloride.

Although the ocular condition may be associated with any chemotherapy agent, the following
chemotherapy agents are contemplated in particular:
Paclitaxel and derivatives thereof, such as Docetaxel
Doxorubicin Hydrochloride,
Irinotecan Hydrochloride,
Fluorouracil,
Imatinib Mesylate, and
Rituximab.

Derivatives of paclitaxel generally include the macrocycle shown below, where derivatives are formed at a hydroxyl moiety.

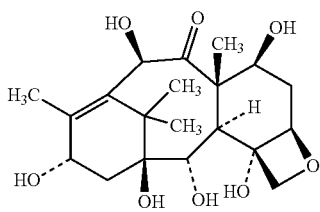

Chemotherapeutic compounds incorporating this structure are thus contemplated. For example, the structures of paclitaxel and docetaxel are shown below.

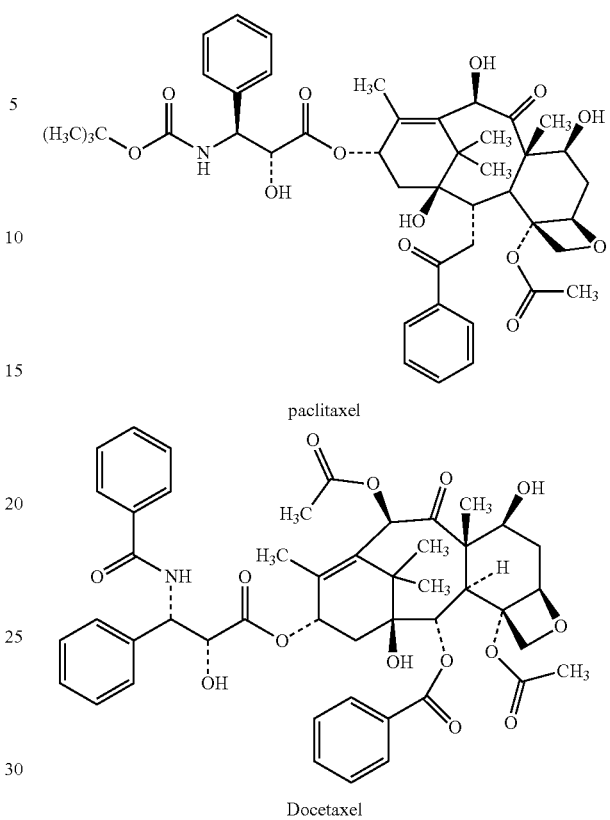

In one embodiment, the chemotherapy agent is docetaxel.

Although the ocular condition may be associated with any immunomodulator, the following
immunomodulators are contemplated in particular:
Interferon alfa-2b, Recombinant
Mycophenolate Mofetil, and
Mycophenolate Mofetil Hydrochloride.

While not intending to limit the scope of the invention in any way, the following therapeutically active agents may cause lacrimal duct stenosis: docetaxel.

While not intending to limit the scope of the invention in any way, the following therapeutically active agents may cause lacrimation:
interferon alfa-2b, recombinant,
doxorubicin hydrochloride,
irinotecan hydrochloride,
fluorouracil,
docetaxel, and
zalcitabine.

While not intending to limit the scope of the invention in any way, the following therapeutically active agents may cause abnormal lacrimation:
mycophenolate mofetil,
mycophenolate mofetil hydrochloride,
imatinib mesylate,
rituximab, and
rimantadine hydrochloride.

While not intending to limit the scope of the invention in any way, the following therapeutically active agents may cause keratitis:
Amantadine Hydrochloride,
Erlotinib,
Bexarotene, and
Voriconazole.

While not intending to limit the scope of the invention in any way, the following therapeutically active agents may cause keratoconjunctivitis:
Capecitabine.

While not intending to limit the scope of the invention in any way, the following therapeutically active agents may cause conjunctivitis:
Risedronate Sodium,
Leflunomide,
Mycophenolate Mofetil,
Oxaliplatin,
Cetuximab,
Ribavirin,
Rituximab,
Basiliximab,
Erlotinib,
Capecitabine,
Doxorubicin Hydrochloride,
Imiquimod,
Amphotericin B, liposomal,
Zolpidem Tartrate,
Glatiramer Acetate,
Epirubicin Hydrochloride,
Saquinavir,
Enfuvirtide,
Imatinib Mesylate,
Gefitinib,
Lamotrigine,
Delavirdine Mesylate,
Rituximab,
Ivermectin,
Palivizumab,
Oseltamivir Phosphate,
Bexarotene,
Docetaxel,
Abacavir Sulfate,
Lamivudine,
Zidovudine,
Voriconazole,
Nevirapine,
Ribavirin, and
Abacavir Sulfate.

Additionally, one or more of the ocular conditions disclosed herein may be associated with the following therapeutically active agents: abacavir sulfate, amantadine hydrochloride, amphotericin B, basiliximab, bexarotene, capecitabine, cetuximab, delavirdine mesylate, docetaxel, doxorubicin hydrochloride, enfuvirtide, epirubicin hydrochloride, erlotinib, fluorouracil, gefitinib, glatiramer acetate, imatinib mesylate, imiquimod, interferon alfa-2b, irinotecan hydrochloride, ivermectin, lamivudine, lamotrigine, leflunomide, mycophenolate mofetil, mycophenolate mofetil hydrochloride, nevirapine, oseltamivir phosphate, oxaliplatin, palivizumab, ribavirin, rimantadine hydrochloride, risedronate sodium, rituximab, saquinavir, voriconazole, zalcitabine, zidovudine, and zolpidem tartrate.

The therapeutically active agent is administered in the usual manner known in the art for the condition being treated.

Alternatively, a therapeutically active agent and cyclosporin A may be administered in a single composition.

Useful compositions are disclosed in the following patent applications, each of which is expressly incorporated by reference herein: U.S. patent application Ser. No. 11/181,409, filed on Jul. 13, 2005; U.S. patent application Ser. No. 11/181,509, filed on Jul. 13, 2005; U.S. patent application Ser. No. 11/181,187, filed on Jul. 13, 2005; U.S. patent application Ser. No. 11/181,178, filed on Jul. 13, 2005; U.S. patent application Ser. No. 11/181,428, filed on Jul. 13, 2005; U.S. patent application Ser. No. 11/255,821, filed on Oct. 19, 2005; U.S. patent application Ser. No. 11/161,218, filed on Jul. 27, 2005; and U.S. Provisional Patent Application Ser. No. 60/727,684, filed on Oct. 17, 2005.

In one embodiment, cyclosporin A is administered in the form of Restasis®, available from Allergan, Inc. The cyclosporin A is administered twice a day as indicated on the package insert.

Although there has been hereinabove described pharmaceutical compositions for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the present invention as defined in the appended claims.

What is claimed is:

1. A method of treating keratoconjunctivitis, the method comprising the step of administering cyclosporin A to a mammal in need thereof, wherein the mammal is suffering from keratoconjunctivitis associated with the use of a therapeutically active agent comprising capecitabine.

2. The method of claim 1, wherein the composition comprises cyclosporin A at a concentration of about 0.05%.

3. The method of claim 2, wherein the composition further comprises castor oil, polysorbate 80, and high molecular weight co-polymers of acrylic acid and a long chain alkyl methacrylate cross-linked with allyl ethers of pentaerythritol.

4. The method of claim 2, wherein the cyclosporin A is administered to the mammal before the mammal receives the therapeutically active agent.

5. The method of claim 2, wherein the cyclosporin A is administered to the mammal after the mammal begins to receive the therapeutically active agent.

6. The method of claim 2, wherein the cyclosporin A is administered to the mammal after the mammal ceases to receive the therapeutically active agent.

* * * * *